(12) United States Patent
Belz et al.

(10) Patent No.: US 7,820,103 B2
(45) Date of Patent: Oct. 26, 2010

(54) CHIP BASED DIAGNOSTIC DEVICE

(75) Inventors: Renato Belz, Emmenbrucke (CH); Haack Carsten, Cham (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 846 days.

(21) Appl. No.: 11/168,122

(22) Filed: Jun. 28, 2005

(65) Prior Publication Data

US 2006/0002818 A1 Jan. 5, 2006

(30) Foreign Application Priority Data

Jul. 2, 2004 (EP) .................................. 04015573

(51) Int. Cl.
*G01N 21/00* (2006.01)
(52) U.S. Cl. ........................... 422/58; 422/57; 422/100; 422/102; 422/104; 436/72; 436/177; 435/6; 435/286.2; 435/287.9
(58) Field of Classification Search .................... 422/57, 422/58, 100, 102, 104; 436/72, 177; 435/6, 435/286.2, 287.9
See application file for complete search history.

(56) References Cited

U.S. PATENT DOCUMENTS

| | | | | |
|---|---|---|---|---|
| 2,017,581 A | 2/1937 | Rosenberg et al. | ............ | 40/152 |
| 5,265,358 A | 11/1993 | Borod | ......................... | 40/155 |
| 5,364,790 A | * 11/1994 | Atwood et al. | ........... | 435/287.2 |
| 5,546,685 A | 8/1996 | Gallagher | .................... | 40/768 |
| 2004/0106130 A1 | 6/2004 | Besener et al. | ................. | 435/6 |

FOREIGN PATENT DOCUMENTS

| | | |
|---|---|---|
| EP | 1 161 989 A1 | 12/2001 |
| EP | 1224976 A1 | 7/2002 |
| EP | 1 281 440 A1 | 2/2003 |
| EP | 1 419 821 A1 | 5/2004 |
| EP | 1224976 B1 | 8/2006 |
| GB | 2 163 287 A | 2/1986 |
| WO | WO 01/45843 A2 | 6/2001 |

* cited by examiner

*Primary Examiner*—Lyle A Alexander
*Assistant Examiner*—Dennis M White
(74) *Attorney, Agent, or Firm*—Vivien Banholzer; Robert W. Mann

(57) ABSTRACT

A diagnostic device comprising a sample inlet and a processing chamber having a window portion and a flat carrier having front surface, a back surface and one or more side surfaces, said front surface facing said processing chamber, said front surface having an active surface containing a diagnostic reagent immobilized to said active front surface and an extended front surface, wherein said window portion further contains a rim portion facing said extended front surface sealing said chamber versus said carrier through said extended front surface.

13 Claims, 8 Drawing Sheets

CHIP BASED DIAGNOSTIC DEVICE

BACKGROUND OF THE INVENTION

This application claims the benefit of priority under 35 U.S.C. §119 of EP Application 04015573.1, filed Jul. 2, 2004, the contents of which are hereby incorporated by reference.

1. Field of the Invention

Subject of the present invention is a diagnostic device for determining analytes, a method for determining analytes using said device, a method for the assembling said device and an instrument for determining the presence of analytes using said devices.

2. Description of the Related Art

The invention is useful in the field of analytics, wherever a device containing immobilized reagents bound to an inner surface of said device are to be contacted with a sample to bind a component of said sample to said device. Particularly, the invention is useful in the field of diagnostics, particularly molecular diagnostics, e.g. the analysis of nucleic acid or protein components in samples such as human body fluids or in environmental samples.

Due to the progress achieved in increasing the sensitivity of assays by amplifying nucleic acid sequences, for instance by the Polymerase Chain Reaction (PCR), as disclosed in EP 0 201 184 and subsequent detection as disclosed in EP 0 200 362 molecular diagnostics has been established as a tool to determine nucleic acid containing parameters, like viruses and bacteria, for instance Hepatitis B virus and HIV. PCR based assays were developed using the so called heterogeneous format as disclosed in EP 0 420 260. In those assays, exemplified in Roche's AMPLICOR assays, nucleic acid sequences of a nucleic acid of a defined analyte, like Hepatitis B virus, are amplified and immobilized on so called capture probes contained in a tube. Due to the slow diffusion of nucleic acids to the capture probes, the immobilization required some time to come to completion. This disadvantage was avoided by the so called homogenous assays that did not need immobilized probes for the detection. An exemplary method is disclosed in EP 0 543 942.

Instruments for performing PCR were developed to conveniently perform the required thermal cycles needed to anneal the primers to the target nucleic acid, extend the primers using the target nucleic acid as a template, and separate the nucleic acid strands to provide single strands that can again bind the primers. A thermocycler useful to conduct thermocycles is disclosed in EP 0 236 069.

Due to the capacity of PCR to amplify nucleic acid sequences which are present in samples in only minute amounts and to amplify different sequences in one sample, assays were developed to amplify and detect several analytes or parameters independently in parallel. Particularly, if more then ten analytes are suspected to be contained and detected in one sample, those assays require the use of a corresponding number of probes, preferably immobilized to separate sites of a solid surface. The manufacture of chips containing a large number of different binding agents is disclosed in EP 0 476 014.

A device for holding chips and conducting analytical reactions in said device were proposed in EP 1 161 989. A first method for processing liquids in said device is disclosed in EP 1 226 863. In this method, a cartridge containing a chip is moved back and forth to mix the liquid contained in said cartridge. In EP 1 224 976 there is described a method for mixing a cartridge wherein the cartridge is swung back and forth to force the liquid to pass the surface of the chip. Those devices have very thin cavities in order to avoid transport of liquid from large distances to the surface of the chip. Thin cavities have the disadvantage that filling with liquid requires relatively complicated inlet and outlet channels and adapters to connect the inlet and outlet channel to a fluid system.

In EP 0 695 941 there is disclosed a flat device containing a chip having a flat cavity, inlet and outlet channels being arranged on the flat surface of the device. Again, the device is difficult to fill because the inlet and outlet channels need to be connected tightly to the instrument. EP 695941 describes a device in which a flat carrier is fixed to a body of a device using an adhesive which is applied to a gap around the flat carrier and the body of the device. This requires aligning the carrier and the device prior to applying the adhesive. Adhesives generally release organic solvents that may harm the reagents on the carrier. U.S. Pat. No. 6,043,080 describes a flat device containing a chip. This device again suffers from the same disadvantages.

Another device for holding chips is disclosed in EP 1 419 821. Because this device has a thicker cavity, diffusion of components of the liquid sample contained therein to the active surface takes too long for routine diagnostics. The reference describes the use of vortexing the liquid sample for mixing.

The devices presently known have the disadvantage that they are either relatively difficult to manufacture, do not provide reliable retaining of the sample and reagents or use adjuvants that may harm the reagents contained on the carrier.

SUMMARY OF THE INVENTION

Figure 1:
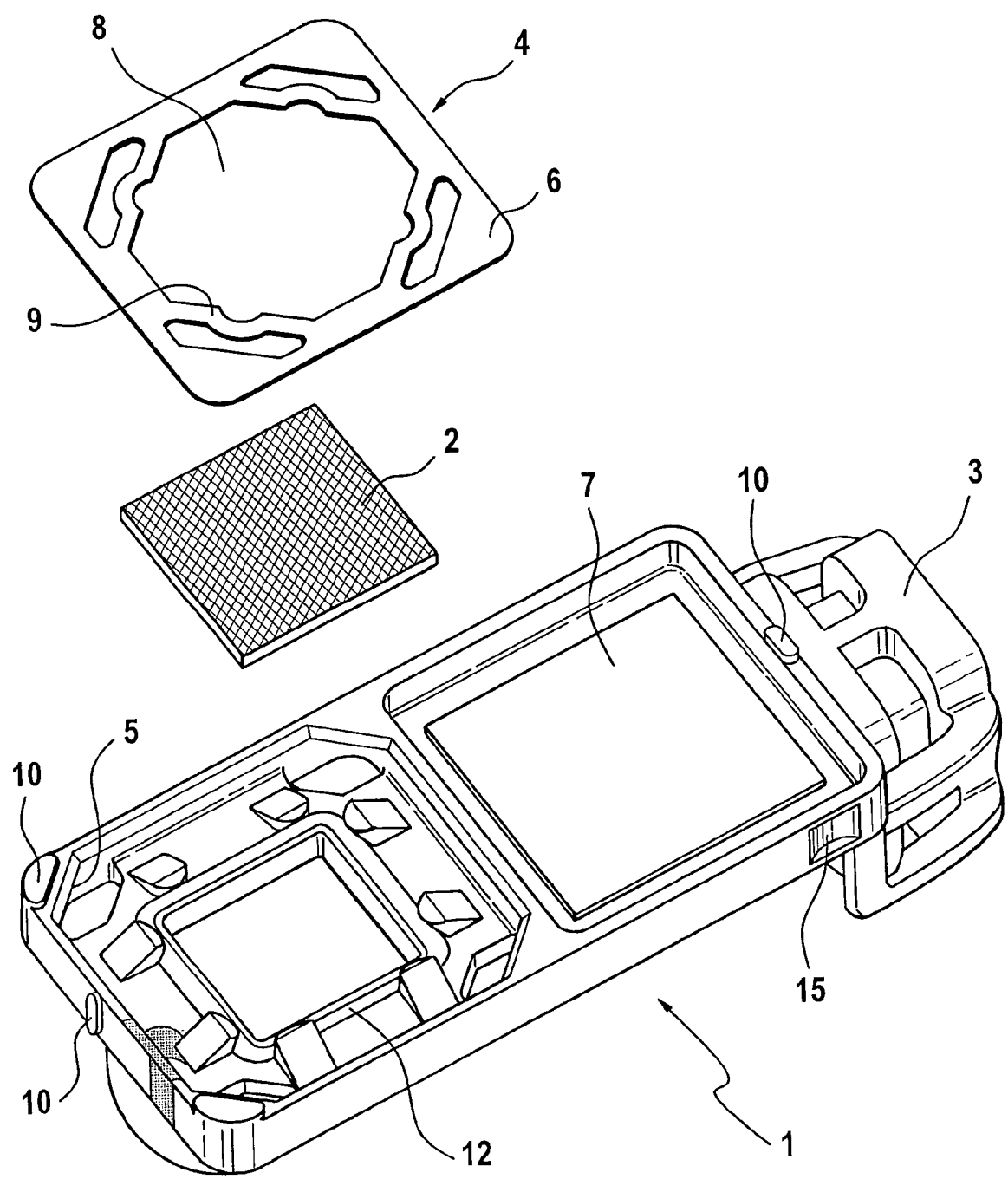
In FIG. 1 there is shown a device (1) according to the invention containing a chip (flat carrier (2)) having immobilized reagents on its surface in exploded view.

In a first embodiment, the invention is directed to a diagnostic device comprising a sample inlet and a processing chamber having a window portion and a flat carrier having front surface facing said processing chamber, said front surface having an active surface containing a diagnostic reagent immobilized to said active front surface and an extended front surface, wherein said window portion further contains a rim portion facing said extended front surface sealing said chamber versus said carrier through said extended front surface further comprising a locking frame to push the carrier towards said rim portion.

In another embodiment, the invention is directed to a method for assembling a diagnostic device comprising a processing chamber having a window portion and a flat carrier having front surface, a back surface and one or more side surfaces, said front surface having an active surface containing a diagnostic reagent immobilized to said active front surface and an extended front surface, comprising the steps of provviding a device comprising a processing chamber having an open window portion said window portion, further containing a rim portion, positioning said device, providing a flat carrier placing the front surface of the carrier on to the rim portion such that the front surface faces the processing chamber and the rim seals said chamber against the carrier through the extended front surface, and fixing the carrier to the device with a locking frame.

In another embodiment, the invention is directed to a method for determining the presence of an analyte in a sample in an instrument comprising the steps of providing a device according to the invention, positioning the device within the instrument, placing the sample into the device such that the sample is in contact with the active surface of said carrier, reacting the sample analyte with the diagnostic reagent, determining the results of the reaction as a measure of the presence of the analyte in the sample.

In another embodiment, the invention is directed to a diagnostic instrument for determining the presence of an analyte in a sample, comprising:

one or more devices according to the invention, a module for entering a sample into the device, and a module for determining the results of the reaction of analytes in the sample with the reagents Another subject of the invention is an article of manufacture for locking a flat carrier to an analytical device comprising a substantially rectangular frame and two or more clips spanning the corners of the rectangle, the clips being more flexible then the frame.

DETAILED DESCRIPTION OF THE INVENTION

Chips for analyzing components of a sample on their surface are well known, for example from EP 0 476 014. They are usually flat plates made from glass or other material inert to the sample and the reagents used to react with the sample and its components. The chip or carrier may have side dimensions of less than 20 mm. In the present invention, it is possible to analyze reactions taking place on carriers having sides of even less than 6 mm. One of their sides, preferably the front side, is at least partially coated by reagents that are designed to bind the components of the sample to be analyzed, if present. The area of said side which is covered by said reagents is from about 4 $mm^2$ to about 2 $cm^2$ and is called active surface. Preferably, the surface covered is flat. The binding reagents are preferably specific for the components to be analyzed. In case of antibodies to be determined, the binding reagent may be an antigen which can be bound by the antibody. For the analysis of nucleic acids, the binding reagent may be a nucleic acid comprising a sequence which can hybridize to the nucleic acid to be determined. In case of nucleic acids, the nucleic acids immobilized to the surface are usually oligonucleotides, i.e. chemically synthesized polynucleotides. Methods for their synthesis are disclosed in EP 0 476 014. Depending upon the number of analytes to be determined in the device the corresponding number of different binding reagents is immobilized to the surface.

The reagents are conveniently arranged in a geometrically fixed and defined manner.

Preferably, ten or more, more preferably between hundred and one million, different binding reagents are immobilized on one chip. Those arrangements are frequently called arrays. When manufacturing the carrier, there is inevitably a part of the front surface which is not covered by the binding reagents. This part of the front surface is called the extended front surface. Usually, it surrounds the active surface. It may have a band width of less than 3 mm, preferably of less than 1 mm. Furthermore, the carrier conveniently has a back surface and side surfaces. The back surface points to the outside of the device and is accessible to detection means, like optics, through a window as outlined in the following.

The chip preferably is transparent for radiation used to detect any signal created or bound to the surface of the chip pointing to the interior of the cavity.

The device according to the present invention has a generally tubular body with a bottom wall, side walls and an upper opening which can be closed by a cap (3) or sealing. The body preferably has a cavity with a volume of 10 to 800 μl preferably 20 to 200 μl. This cavity is used as a process chamber to treat the sample fluid. Thus, it is designed to be at least as large as the volume of sample fluid to be transferred into the device for treatment. Preferably, the volume is at least 10% larger than the volume of the liquid to be transferred. The cavity further has a form allowing the sample liquid to fully contact the binding reagents on the surface of the chip. The chip is preferably located at one of the side walls of the device, such that the cavity is accessible for a pipetting device for aspirating and dispensing the sample liquid or/and any reagents without the pipetting contacting the surface. The shape of the cavity is such that there is a distance of at least 1.5 mm from the binding reagent bearing surface to the nearest wall of the cavity. Preferably, the cavity has a diameter of at least 3 mm in the region of the chip. The length of said cavity from the bottom to the opening is at least 5 mm. The body of the device is preferably made from thermoplastic polymers, more preferably from polycarbonate, prepared by injection molding.

In a preferred embodiment, the cavity has the shape of a cuboid having side lengths which are equal or of the same order of magnitude. That cuboid has a side length of 3 mm or more.

In a preferred embodiment, the device comprises means (15) to pick and transport the device for instrumentation, automation or assembly purposes, which are located on the upper part of the device, preferably in pairs oppositely arranged at the sides of the device. These picking and transportation means are arranged such that the carrier itself, the device assembly process and the liquid application through the device opening is not affected. Such means for picking and transport are preferably selected from the group of grooves, recesses, projections, noses and protrusions formed from or in the surface of the device. The means are formed at an accessible site on the device such that engagement with a gripping device on an instrument designed to pick and transport said device is possible. Most preferably, the means is a groove in a surface of the device. Such groove preferably may be between 0.1 and 5 mm deep and preferably covers an area of between 0.01 and 0.5 $cm^2$ of the surface. The means preferably are within the upper part of the device, i.e. within the half near to the cap.

The device also comprises means (10) for accurately positioning the device and the carrier relative to device holders or other device interfaces. An illustrative example of how a device can be held in an instrument is given in FIG. 1. These positioning means are arranged on the device such that all degrees of freedom of the device are fixed and the position of the active surface of the carrier is defined with respect to the device during processing, detection or assembly of the device.

For identification and process control in instruments the device comprises as integral part a plane and printable space (7) for labeling, e.g. with a barcode, such that the labeling process does not interfere with the carrier itself or with the fixation process of the carrier and can be carried out during or after the device assembly process. For automation and assembly purposes in a preferred embodiment the printable space is on the same face of the device as the carrier.

In a preferred embodiment, the device of the present invention has a geometry similar to the device according to EP 1 419 821, which is hereby incorporated by reference to disclose the characteristics and the manufacture of said device. This device has the advantage that mixing by vortexing is very efficient in said chamber.

The cap of the device is preferably fixed to the device to close the opening if not punched. The fixation is preferably so tight that the cap cannot be removed without destruction of either the device or the cap. A preferred method and means to firmly fix the cap to the device is by snap-in connection. The cap may comprise means to pick the cap and the device up by a transfer module. Cap forms suitable for being picked up by automated transfer means are disclosed in EP 907083, which is hereby incorporated by reference. In a preferred embodiment, the cap is firmly and irreversibly affixed to the device.

In a preferred embodiment, the cap comprises a membrane for separating the processing chamber from the environment. More preferably, the membrane is pierceable. Materials for such pierceable membranes include silicone and polymer. Most preferred are self-sealing materials, such as elastomers, most preferred TPE (thermoplastic elastomer, melt-processable rubber). If pierced, the material should retain more than 90% or the liquid when heating for 16 hours for on 60° C. The cap is preferably manufactured by 2-component-injection-molding. A perfect fit to the processing chamber can be achieved, if the diameter of the cap in the region facing the chamber is slightly larger than the inner diameter of the chamber in this region, such that a slight pressure is maintained on the inner diameter of the chamber.

Figure 2:
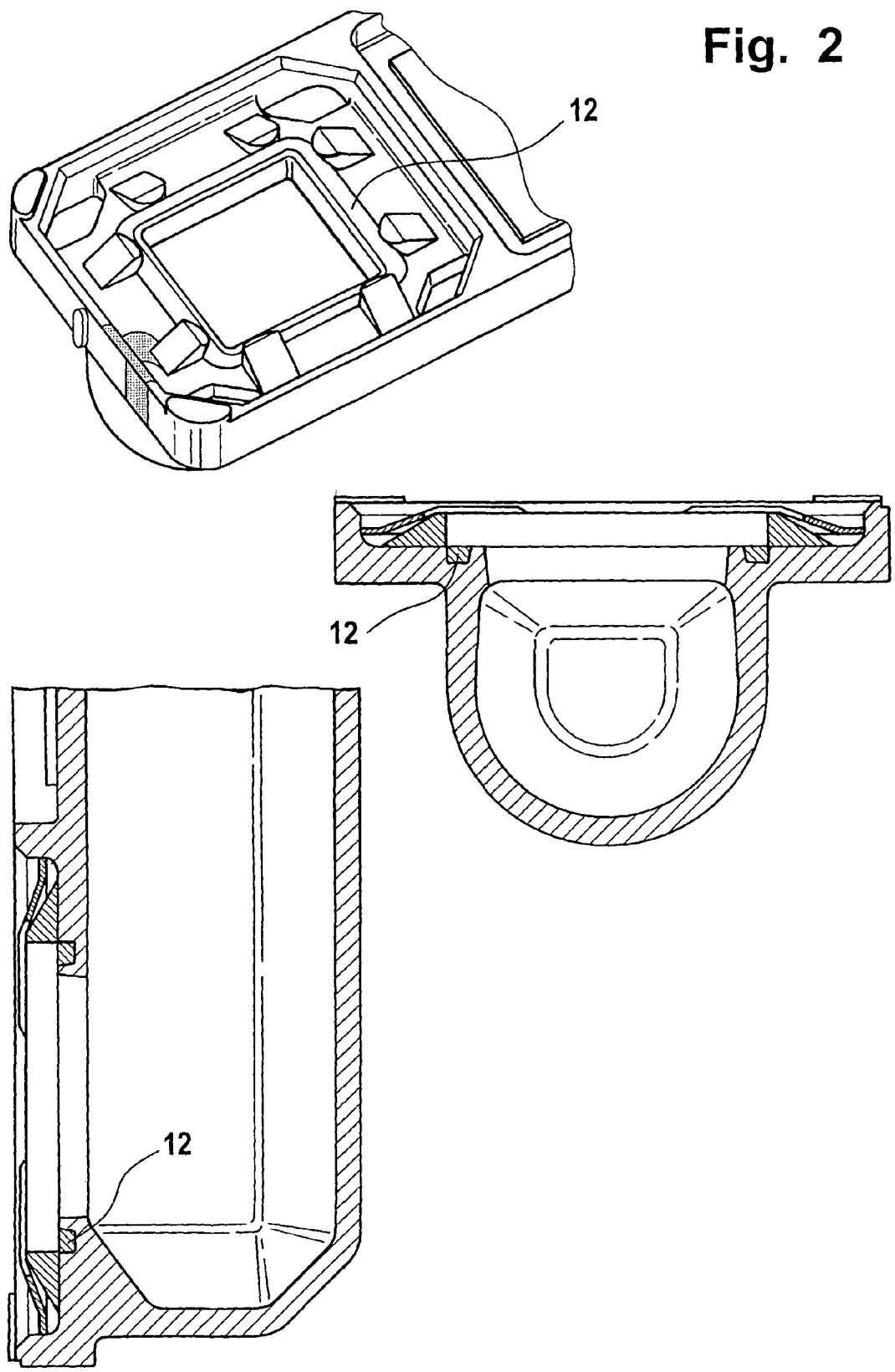
FIG. 2 shows cross sections of an exemplary device particularly showing the rim (12) according to the invention and the bottom part of the device without the chip inserted. The light grey area extending from the rim to the exterior of the device marks the injection path of the material used to produce the rim.

Preferably, the rim portion contains a circumferential wall made of an elastic material. Furthermore, materials preferentially are inert to clinical samples and reagents used for hybridizing and detecting nucleic acids. Materials which are inert to irreversible changes of shape at temperatures between 4 and 95° C. are preferred. Such material is selected from the group of silicone or polymer, most preferred TPE (thermoplastic elastomer). These materials have the advantage that they are melt-processable and can be produced within the same process as the body of the device. Further preferentially, the rim has a planar or linear profile that fully reflects the shape of the surface of said chip. As the surface of the chip generally is flat, the profile of the rim is essentially linear and essentially surrounds the active surface of the chip without interruption. In FIG. 3, exemplary profiles of the rim are given. Preferred profiles do not exhibit edges at the contact to the surface of the chip. More preferably, the cross section of the rim pointing to the surface of the chip is essentially curved. Exemplary cross sections are shown in FIG. 2.

The rim can conveniently be prepared separate from the device, and then combined with the device, for instance by preparing a ring of rim material and a device having a recess to receive the ring and then pressing the rim ring into the recess in the device. In a more preferred mode, the device having a recess is prepared as conventional, and the rim is then injection molded into the recess of the device using a form.

Another preferred feature of the device according to the invention is a dead stop provided on the device in the area opposing the extended front surface. This is used to define a position of the carrier in the device, both for detection accuracy and tightness of the fit. The dead stop is positioned such that when the carrier is pushed towards the rim and compresses the rim, the carrier stops proceeding when reaching the dead stop position. The dead stop preferably surrounds the rim opposing the extended front surface, but it needs not be sealing tightly. Preferably, it is made from the same material as the device and an integral part of the device. The position of the dead stop together with the positioning means defines and references the position of the carrier within the device and thus within the instrument.

In a preferred embodiment, the device according to the invention comprises a locking frame to push the carrier towards the rim portion. By this feature, the carrier is pressed towards the rim portion such that there is no space between the rim and the opposing part of the surface. Moreover, the locking frame provides that the rim portion is compressed by the pressure asserted against the carrier. This makes sure that the rim fits the surface over the full temperature and pressure range such that no liquid escapes the device through the connection of the rim and the carrier. The pressure asserted against the surface preferably is between 1 and 1000 mbar. The locking frame further allows access of electromagnetic radiation to and from the active surface of the carrier. Thus, the frame may have a window in its structure resembling the shape of the active surface or slightly larger, i.e. up to 100% larger. The smaller the part of the frame covering the back surface of the carrier, the better is the frame in view of the high costs of the carrier and the desired compactness of the device. The window has substantially rectangular or square inner borders, mainly reflecting the outer borders of the active surface of the carrier. Furthermore, the locking frame preferably has a substantially flat structure. Preferably, at the inner borders of the window, it protrudes from the back surface of the carrier by less than 0.3 mm, more preferably between 0.01 and 0.3 mm. The locking frame preferentially is made from a material that is inert over the temperature range given above for at least 24 months against irreversible deformation and loss of pre-tension of more then 10%, more preferable more than 5%. The material preferably has an extension coefficient of less than 20 μm/m° C. The locking frame can be made of a single material or can be a composite. Preferably, the frame contains a metal portion, preferably made from steel, most preferably stainless steel, as metals generally have high tension retention over the full temperature range and are stable against destruction. Other materials useful for construction of locking frames are plastics. Particularly preferred are composites of metal and plastics, i.e. steel and polymer. Preferred, the locking frame is made of steel 0.1 mm thick.

The locking frame is another subject of the invention. It is an article of manufacture used to fix the carrier to the rim portion of the device. It comprises a substantially rectangular frame and two or more clips spanning the corners of the rectangle being more flexible then the frame.

The term rectangular is meant to describe a geometric form which has at least 4 sides, preferably just four sides. Those sides may have identical (forming a square) or different length. Preferably, adjacent sides form 90° angles, forming corners. Thus, the frame preferably has 4 corners. Further, the frame may show recesses or protrusions on the sides or the corners. Those recesses or/and protrusions can advantageously be used as means for positioning the locking frame within the device. Another use is to adjust rigidity of the frame to provide the flexibility to twist the frame such that it can snap in into respective recesses (5) of the device while maintaining a force to stay within the recesses (5).

The locking frame comprises means to push the carrier to the body of the device if the locking frame is inserted into the device. This is preferably done by clips that span corners of the frame. Preferably, the clips are more flexible than the frame, such that the clips get deformed when the locking frame is inserted into the device. The force applied to the carrier by the clips therefore can be described as a kind of spring force. While for some embodiments not needing high pressure it may be sufficient to use two clips, i.e. on opposite corners of the frame, it is highly preferred to use three or even four clips spanning the corners, i.e. spanning all corners.

In a preferred embodiment, a clip is a brace bridging a corner by connecting two adjacent sides of the rectangles. Even more preferred, there is a gap between each clip and the corner it spans. This gap can have different functions in the locking frame. In a first embodiment, it can be used to position the locking frame on the device, for example by inserting a guide into the gap, forcing the locking frame into the desired position.

Fixing of the locking frame in the device can be done by means provided on the locking frame. Those fixing means can be at virtually all positions that do not hinder the optical detection on the active surface of the carrier. Most preferred is the area of the back surface opposite the extended front surface on the carrier. Preferred means are provided by or on the corners of the frame. In a very preferred embodiment, the corners themselves are used to fix the frame to the device. For this, the corners have a shape or the corresponding site at the device has a shape such that they fit together to fix the frame. However, there are other positions on the frame that can be used to fix the frame to the device, either of the outer sides of the frame or within the inner borders of the frame. In this case, most preferably, the gaps formed between the clips and the corners of the frame are used to fix the frame. This can be done by providing means at the device that protrude into the gap, and that even contain an element for snap-in connection with an element on the frame, preferably on the perimeter of the gap.

Figure 3A:
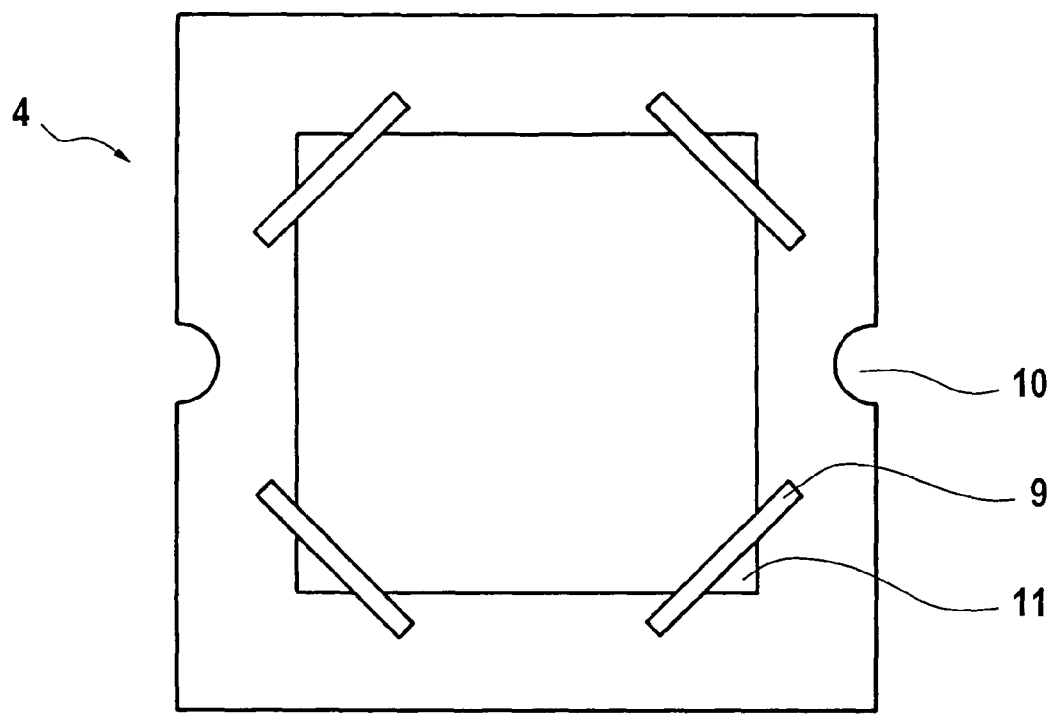
FIG. 3a schematically shows a locking frame construction.
Figure 3B:
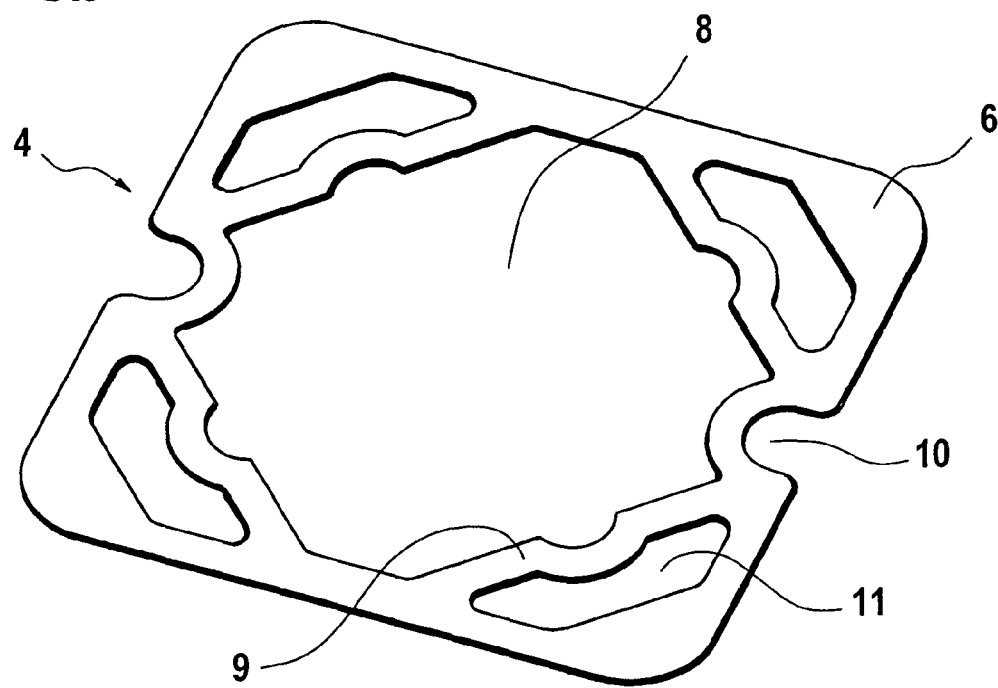
FIG. 3b shows an exemplary locking frame (4).

To achieve fixing the carrier to the device, the clips overlap with the back surface of the carrier outside of the active surface, preferably on the corners of the carrier. It is preferred that only the clips overlap the carrier, not other parts of the locking frame. In result, a window is formed by said frame and the clips which is larger then 99%, more preferably larger than 99.5%, of the surface of the flat carrier. The window further preferably has substantially round corners, pointing to the corners of the frame. Substantially round means that the corner does not contain angles of more than 70°, more preferably not wider than 45°. Most preferably, the corner does not have macroscopic angles, but is smoothly curved. The advantage for such form of the corner is that substantially round corners allow most efficient use of the window for detecting signals from the active surface of the carrier. Working examples of such locking frames (4) are shown in FIGS. 3a and 3b. Most preferred is the article of FIG. 3b, as it is flat and easily manufactured and handled.

The article of manufacture can be prepared by methods as generally known for manufacturing flat articles. The particular method depends on the material used for the manufacture. In case of metal frames, the locking frame can be punched out of a metal plate. Another mode is etching the form from a metal plate. In case of a composite locking frame, manufacturing processes may comprise several subsequent steps, including injection molding, punching or/and etching.

It has proven to be particularly advantageous, if the locking frame is flat and not protruding more than 1 mm, more preferably not protruding for more than 0.5 mm over the overall plane on the side of the device exhibiting the carrier. This is very advantageous for convenient detection of the signal provided on the active surface of the carrier. The irradiation is preferably done by confocal radiation. Detection of the resulting light may be done by CCD. Such method uses a conus for impinging light focused on specified locations on the inner surface of the carrier (optical aperture). Thus, the window in the frame needs to be larger than the active surface dependent upon the angle of the impinging light beam.

Preferred frames are shown in FIG. 1, FIGS. 3a and 3b.

In FIG. 1, on the left, a frame is shown that comprises a window (8), lips (6) for engaging to recesses (5) in the device (1) and retainers (9) for contacting the carrier. In FIG. 3a, a schematic drawing shows the frame (4), retainers (9), the window (8) and positioning means (10). The frame is the interface to the body of the diagnostic device and is connected with the body. The frame also is support of the elastic (metal) braces. The elastic (metal) braces are the interface to the carrier (chip) and are fixing the device with a constant time-independent (no creep) force on the rim. The metal braces are connected to the frame. The positioning markers allow for a well defined connection of frame and process chamber and a well defined connection of metal braces and diagnostic device.

The locking frame can be prepared according to known methods. If it is made from metal, a metal plate is conveniently cut in the form, i.e. punching a piece having the desired outer shape and the window portion from a thin metal plate, and then the piece is pressed to provide the final three dimensional shape. If made from a composite, any metal parts are formed as described as above, and then the plastic part is injection molded surrounding the metal part.

The locking frame preferably comprises means for reversibly or irreversibly attaching it to the device. This can be realized by parts fitting into respective recesses (5) in the device. Preferably, the locking frame has snap-in means to fit into recesses (5) of the device such that the frame cannot be removed from the device without irreversibly destroying the device or the frame. Even if parts have to be destroyed they can be separated after use and therefore disposed separately. This is another advantage over glue or melting connections regarding possible waste separation requirements.

The invention has the advantage over melting in the carrier with thermoplastic materials that the thermoplastics tend to deform at higher temperatures and thus are not reliably sealing. Furthermore, they have to be heated together with the carrier to tightly seal the carrier to the device. This may destroy or at least affect the binding properties of the active surface. Glues generally have the disadvantage that they tend to set free monomers which interfere with the detection conditions in the device.

FIG. 3 shows some embodiments of advantageous locking frames. In FIG. 3a, the preferred and the essential features of the locking frame (4) are shown schematically. Reference is made to the reference numerals below. In FIG. 3b, a particularly advantageous locking frame is shown. It is essentially flat and has areas that have the functions as described above. Particularly, the window has round corners provided by the form of the clips facing the window.

Figure 5A:
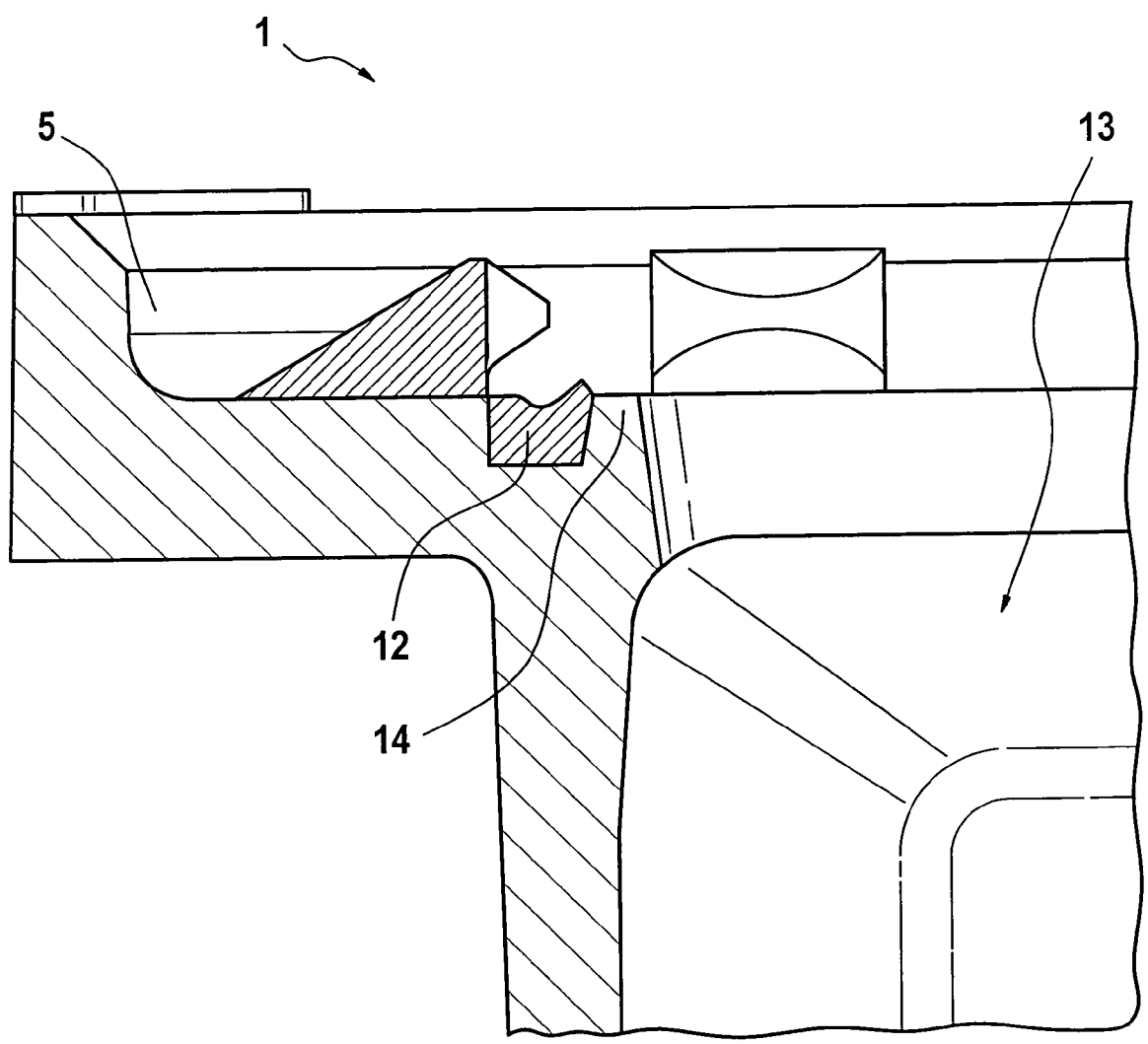
FIGS. 5a and 5b show the device according to the invention in a view cut through the corners of the carrier in unassembled and assembled state.
Figure 5B:
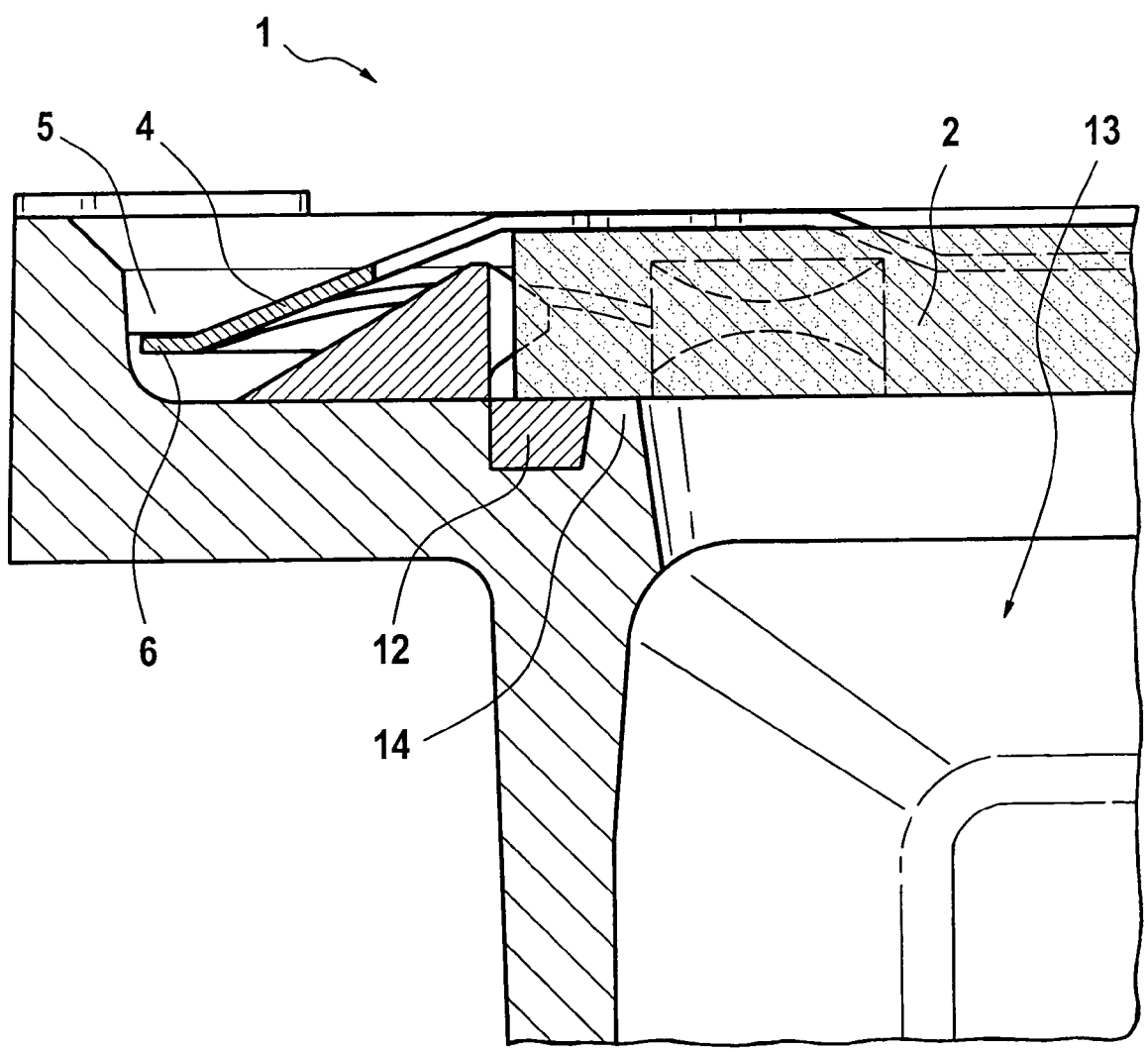

FIG. 5a shows a device (1) according to the invention in cut view without the carrier in position. The rim protrudes over the deadlock. FIG. 5b shows the same device in the area close to the corners (6) of the flat carrier (2), cutting the extended front surface and the active surface facing the processing chamber (13). The locking frame pushes the carrier (2) towards the dead stops (14) and the rim (12). The recesses (5) in the device fix the locking frame (4) at the 4 corners (6) of the locking frame (4) and are set up such that they can be produced by injection molding. It can be seen that the rim portion (12) surrounds the dead stop portion (14). This is preferred to shield the rim from the majority of the liquid contained in the device.

The next mode of the invention is a method for assembling a diagnostic device comprising a processing chamber having a window portion and a flat carrier having front surface, a back surface and one or more side surfaces, said front surface having an active surface containing a diagnostic reagent immobilized to said active front surface and an extended front surface, comprising the steps of:

providing a device comprising a processing chamber having an open window portion the window portion further containing a rim portion, positioning the device, providing the flat carrier, placing the front surface of the carrier on to the rim portion such that the front surface faces the processing chamber and the rim seals the chamber against the carrier through the extended front surface, and fixing the carrier to the device with a locking frame.

The carrier is preferably fixed to the device by pressing the locking frame towards the device, such that it is retained in a position which fixes the carrier, i.e. such that the locking frame snaps into the recess (5) of the device.

Preferably, by this action by the above mentioned locking frame, the carrier is pressed against the rim portion such that the chamber is sealed against fluid escape. The locking frame is pressed against the back surface of said carrier such that the front surface of the carrier is pressed tightly to the rim of said device. The portions of the locking frame contacting the carrier are preferably retainers (9) on the locking frame, more preferably located at the corners of the window (8). Preferred fixation means are disclosed above. The most preferred fixation is via a snap-in construction such that the lips (6) snap under the recesses (5).

One advantage of the present invention is that it provides reliable and efficient binding, staining or washing in devices containing immobilized binding reagents.

In a preferred embodiment, the device is labeled with carrier and production information, e.g. using a bar code label. In addition, the label can further contain information for identifying each individual device. This enables sample or process identification.

Positioning of the device preferably within an assembly machine, preferably is made using means 15 or/and 10. This enables exact positioning of the carrier relative to the rim and the dead lock.

The status in which the carrier is not yet pressed against the rim portion is shown in FIG. 5a. It can be seen that the rim slightly protrudes over the deadlock, such that when the carrier approaches the dead lock, it first touches the rim portion and only when further advanced versus the dead lock, the rim is deformed until the carrier is stopped by the dead lock. When the carrier is pressed against the dead lock, the rim is in deformed state and may either be compressed or protrude at a site where no pressure is asserted by the carrier. The combination of the rim with the dead lock provides fluid tight sealing of the carrier and exact positioning of the carrier within the device.

In another aspect, the invention provides a method for determining the presence of an analyte in a sample in an instrument, comprising the steps of providing a device according to the invention, positioning the device in the instrument, placing the sample into the device such that the sample is in contact with the active surface of the carrier, reacting the sample with the diagnostic reagent, and determining the results of the reaction as a measure of the presence of the analyte in the sample.

A sample according to the invention can be any liquid which is intended to be subjected to analysis. Usually samples are fluids taken from the human body, like urine, sputum, blood, liquor or fluids derived therefrom, like serum or plasma. Preferred samples are fluids as above, further pretreated for better analysis. Pretreatment steps may be chosen for the group of isolation of components, removal of components from the sample, concentration, dilution, addition of reagents, amplification of components and lysis of components. Those pretreatment steps may have been done manually, be performed on another instrument, or performed on the same instrument. The sample most conveniently is placed into the device by pipetting the liquid into the device through the inlet port. For this purpose, the inlet port may be pierceable for a syringe or a pipette tip. Most preferably, the inlet port is made from a material that if pierced once, retains a small opening, such that it can also act as a gas outlet. Therefore, the inlet port preferably is located in the upper part of the device (FIG. 6) such that the liquid, i.e. the sample does not reach the inlet port and thus cannot escape. Appropriate materials for such pierceable inlet ports are silicone and polymer, preferably TPE (thermoplastic elastomer, melt-processable rubber) that allows for sealing aspects as well as for multiple piercing of the inlet for repeated liquid applications.

In more detail, the method according to the present invention comprises the following steps:

1. load the sample, the reagents and the diagnostic devices
2. run the sample preparation (for example, cleavage by a restriction enzyme to produce nucleic acids of defined length)
3. if time delay cool down and hold samples
4. transfer the sample to the diagnostic device
5. start the hybridization
6. wash
7. start staining
8. wash
9. transfer to a detection station
10. transfer to a waste station One advantage of the present invention is that it provides reliable and efficient binding, staining or washing in devices containing immobilized binding reagents.

Figure 4:
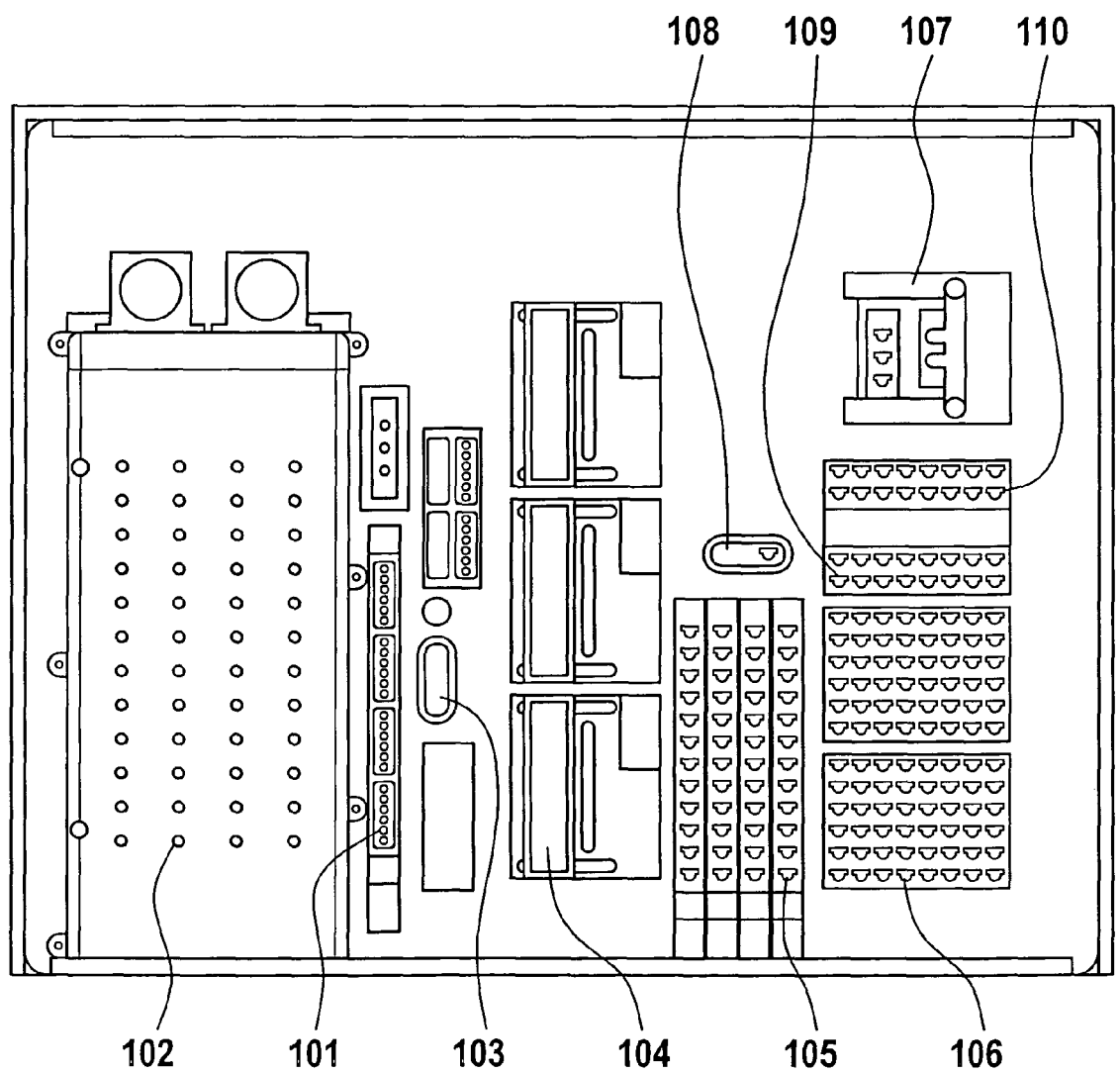
FIG. 4 schematically shows an instrument according to the invention from top view.

The method for automated processing of one or more analytical devices containing immobilized binding reagents according to the invention preferably contains the following steps:

In a first step, the samples are loaded into the sample loading area (101). FIG. 4 shows a rack of 24 sample vessels, in 4 discrete plates, each having 6 cavities to keep a sample in each cavity. For this, the incubator (104) is opened, and the incubator is loaded with sample tubes. Reagents are aspirated from the reagent bottles contained in reagent storage (102). The sample tubes are opened. The reagents are pipetted, dispensed into each of the sample tubes. The sample tubes are closed. The needles are washed. Then the sample tube is incubated at 40° and up to 95° C. During this step the amplified nucleic acids are transformed (cleaved) into shorter pieces. In the staining step, the following steps are performed:

The incubator is opened, reagent is aspirated, the sample tubes are opened, and the reagent is dispensed into the sample tubes. The sample tubes are closed, needles are washed. The mixture is incubated at 40° and up to 75° C.

For binding, the following steps are performed: get sample and hybridization buffer, fill chip disposable through pierceable cap, pick and place device into hybridization station, heat and mix, at 60° C. up to 16 h.

Washing is made as follows: pick and place device into wash station, wash with washing buffer A (multiple times) through pierceable cap, mix during wash procedure, wash needle each time, fill device with stain buffer.

For staining the following steps are performed: pick and place device into stain station, mix during staining.

Another washing is performed as follows: pick and place device into wash station wash with washing buffer B (multiple times) through pierceable cap, mix during wash procedure, wash needle each time, fill device again with stain buffer.

The detection is performed by pick and place device into scanner inlet and start detection.

In a preferred embodiment, the positioning of the device within the instrument is done by means 15 or/and 10 as described above. An exact positioning is essential for exact reading of the signals from the active surface of the carrier.

In another aspect, the invention is directed to a diagnostic instrument for determining the presence of an analyte in a sample, comprising:
- one or more devices according to the invention firmly positioned within said instrument,
- a module for entering a sample into the device,
- a module for determining the results of the reaction of analytes in the sample with the reagents.

For illustration of the invention, preferred details of the instrument are explained by referring to the reference numerals shown in FIG. 4.

Usually, a sample input station defines the position to receive the containers containing one or more sample vessels. Those positions are defined such that the instrument recognizes each position as to receive a defined sample. This sample preferentially is identified by a label, such as a bar code label that can be read prior to the sample entering the instrument or thereafter or concurrently therewith. This is done by a reader located adjacently to or within the sample input station. In the present invention, the sample receiving station has at least 4 positions to receive sample vessels, preferably at least 8, more preferably between 8 and 96 sample vessels. This way, the instrument is capable of handling a corresponding high number of sample fluids without any need to stop other processes occurring within the instrument.

A module for entering the sample to the device may be a part of the instrument which is used to supply the sample to the diagnostic device of the invention. This is preferably done automatically. Convenient means are pipetting means that can be controlled by a computer. Such pipetting devices are generally known and can be used in the present invention. Conveniently, the device comprises a socket for receiving a pipette tip and a pump for applying a slight vacuum to the interior of the pipette tip, such that, if the lower opening of the pipette tip is in contact with the sample, sample is sucked into the pipette tip. After aspirating the sample, the device is moved to the device according to the present invention, inserting the tip of the pipette tip through the inlet port into the device according to the invention. Then, the liquid is released and dispensed into the device. The same is done for any reagents needed for the reaction.

Figure 7:
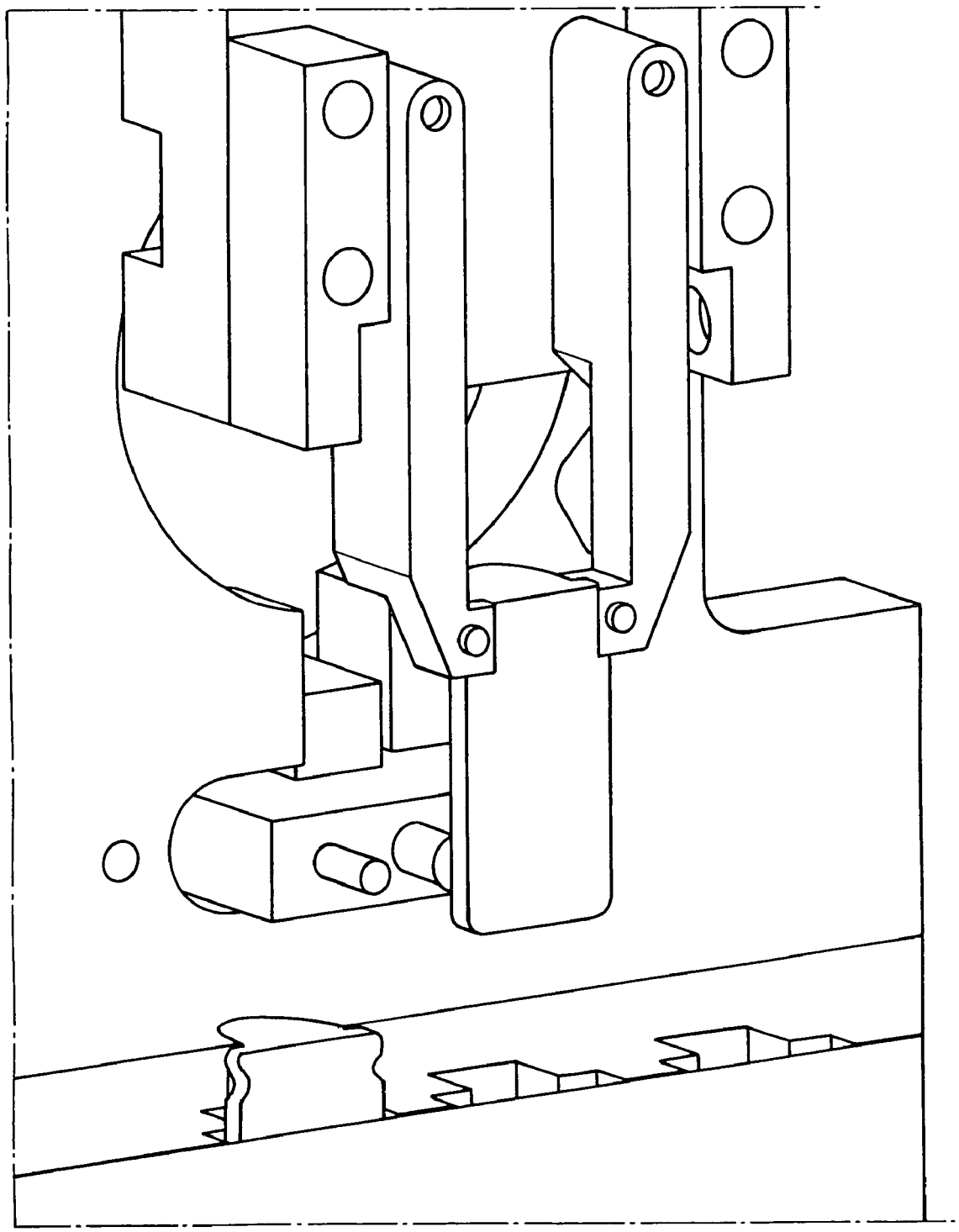
FIG. 7 shows a gripper for the device (1) for instrument automation.

A transfer module according to the invention is a part of the instrument intended to transfer a fluid, for instance a sample fluid or a reagent, or/and to transport a device, either empty or containing any fluid, from one location to another location. Thus, preferred transfer modules comprise a liquid handling unit, like a socket for receiving a pipette tip or a syringe, and/or a gripper for interlocking to a device or a part of a device. Appropriate transfer modules are well known, e.g. from EP 0 907 083. A preferred gripper for the described device is depicted in FIG. 7. FIG. 7 shows also a preferred embodiment of the gripper interface (15) on the upper part of the device as given in FIG. 1.

A treatment station is a station designed for treating the device during the analytical process. It includes a position to maintain the device containing the sample at a defined position within the station. Appropriate positioning means are recesses in the station, defining a holder for the device. In a very preferred embodiment, the treatment station comprises a device carrier, in the following called dispo carrier, which has openings to receive one or more, preferably two or more, most preferably between 4 and 48 devices. The inner form of the recess preferably mimics the outer form of the device, at least in the part of the device which is intended to be treated in the particular treatment station, such that the device cannot unintendedly escape the treatment station during treatment.

Preferred treatment stations are selected from binding stations, staining stations and washing stations, or any combinations thereof, like a combined binding and staining, a combined staining and washing, a combined binding and washing and a combined binding, staining and washing station. The design of said station is determined by its function. Thus, the functions of the treatment station are selected from the function of binding, staining and washing.

In a first preferred embodiment, a first treatment station is a binding station. A binding station preferably provides all conditions needed for efficient binding of components of the sample to one or more of the binding reagents immobilized in the device. Efficient binding preferably is achieved by keeping the sample within the device at a defined temperature. Preferred temperatures for binding nucleic acids to capture probes are between 20 and 95° C., more preferably between 40 and 60° C. For reaching the intended temperature, the binding station preferably has a heating element, like a resistance heater, a Joule heater or a Peltier element. For maintaining a desired temperature, the station may contain isolation means around the device or/and the heater. Such isolation means may be made from polystyrene or other isolating plastics and may be contained within a cover.

In a second embodiment, the treatment station is a staining station. Staining is a process to visualize any components bound to the binding reagents immobilized to the device. It is mainly used in case the components are not directly detectable, but need further reagents to develop a signal. Such reagents may be compounds being capable of binding to the components bound to the device. In an exemplary assay, the components of the sample to be analyzed are nucleic acids labeled with biotin. In this case, staining can be done by contacting the sample with a conjugate of avidin or streptavidin and a fluorescent label. After completion of the binding reaction of biotin to (strept-)avidin the resulting complex will have fluorescent characteristics.

Figure 6:
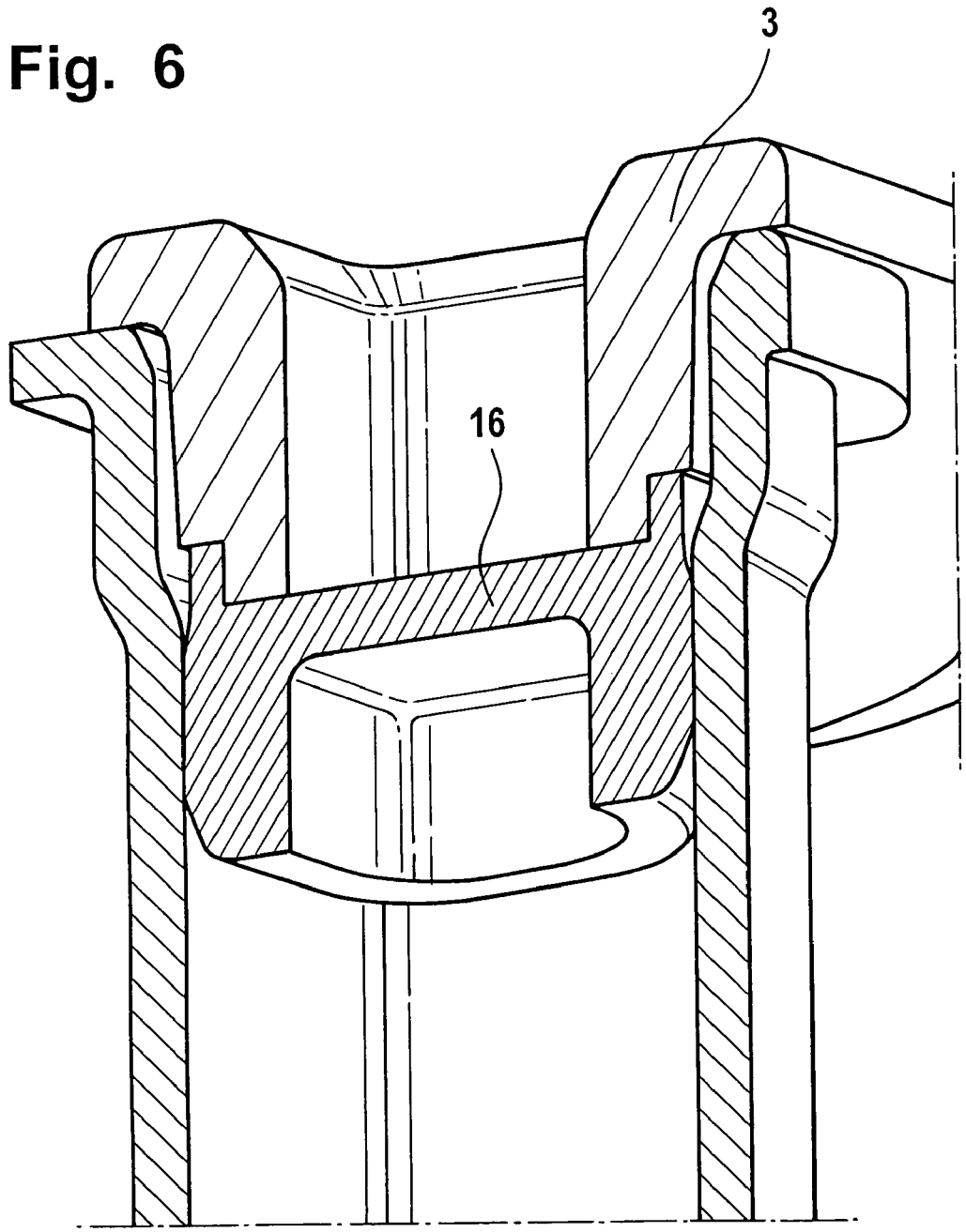
FIG. 6 shows a cross section of the cap (3) with pierceable membrane (16).

In a third embodiment, the treatment station is a washing station. Washing is a process to remove unwanted components of the sample from the bound components. To achieve this, after completion of the binding reaction the liquid is removed from the device, while any components bound by the binding reagents will remain in the device. A washing liquid is added to the device to further dilute any remaining undesired components which may still adhere to the device. The washing liquid is removed from the device together with the undesired components. This process preferably is repeated as often as necessary to remove undesired components to a concentration not interfering with the determination of the intended analyte. The washing liquid has a chemical constitution which does not substantially affect the binding of the analyte to be determined. The liquid is applied directly through the device opening, preferable through a cap (3) with pierceable membrane (16) as shown in FIG. 6. No additional device opening or closing processes or docking to special fluid application stations are necessary.

A detection station is a part of the instrument equipped with a unit for detecting a signal received from the sample upon stimulation of the sample. Means for stimulating a sample comprise irradiation by electromagnetic radiation, for instance light appropriate for exciting a component in the device which is a measure of the presence, absence or amount present of the analyte. In a preferred embodiment, the light is used to excite a label attached to a probe. The signal, i.e. the light returning from the device is then correlated with a reference signal received from a sample with known analyte(s). In a more preferred embodiment, the surface of the chip pointing to the inner of the cavity is scanned for a signal and the locations showing a signal and the intensity of the signal received from each location are identified. Those detectors may also include a confocal scanning microscopic device. Suitable scanning detectors are widely known in the art.

In a preferred embodiment the instrument comprises positioning means located at positions to engage with means 15 or/and 10 of the device. This enables exact reading of signals from the active surface on the carrier as a result of the reaction.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes

REFERENCE NUMERALS

1 Device according to the invention
2 Flat carrier (shown from back surface)
3 Pierceable cap
4 Locking frame according to the invention
5 Recess for keeping the locking frame
6 Lip of the locking frame undercutting the recesses/corner (5)
7 Space for bar code label
8 Window
9 Retainer/clip
10 Adjustment recesses/positioning means
11 Gap
12 Rim
13 Processing chamber
14 Dead stop
15 Gripper interface
16 Pierceable membrane
101 Sample input module
102 Reagent input module
103 Waste disposal position
104 Incubator
105 Device input module
106 Hybridization station
107 Washing station
108 Detection station
109 Staining station
110 Rinsing station While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes

The invention claimed is:

1. A diagnostic device comprising a sample inlet and a processing chamber having a tubular body, a window portion and a flat carrier having front surface facing said processing chamber, said front surface having an active surface containing a diagnostic reagent immobilized to said active front surface and an extended front surface, wherein said window portion further contains a rim portion facing said extended front surface sealing said chamber versus said carrier through said extended front surface, further comprising a locking frame to push the carrier towards said rim portion up to a dead stop position, said locking frame having a substantially flat structure comprising clips spanning corners of said frame, said clips being more flexible than the frame, wherein each clip is a brace bridging a corner by connecting two adjacent sides of the frame, and wherein there is a gap between each clip and the corner it spans.

2. The device according to claim 1, wherein said rim portion contains a circumferential wall made of an elastic material.

3. The device according to claim 1, wherein said locking frame is flat containing metal parts.

4. The device according to claim 1, wherein the sample inlet is closed by a cap comprising a pierceable membrane.

5. The device according to claim 1, wherein the processing chamber is a mixing chamber.

6. A method for assembling a diagnostic device according to claim 1, comprising :
providing a device comprising a processing chamber having an open window portion, said window portion further containing a rim portion,
positioning said device,
providing said flat carrier,
placing the front surface of said carrier on to said rim portion such that said front surface faces said processing chamber and said rim seals said chamber versus said carrier through said extended front surface,
providing a locking frame having clips spanning corners of said frame, wherein each clip is a brace bridging a corner by connecting two adjacent sides of the frame, and wherein there is a gap between each clip and the corner it spans and
pressing said locking frame towards the device such that it is retained in a position that fixes the carrier.

7. The method of claim 6 further comprising labeling the device.

8. A method for determining the presence of an analyte in a sample in an instrument comprising the steps:
   providing a device according to claim 1, positioning said device within said instrument,
   placing said sample into said device such that said sample is in contact with the active surface of said carrier,
   reacting said analyte with said diagnostic reagent, and
   determining the results of said reaction as a measure of the presence of said analyte in said sample.

9. The method of claim 8, further comprising the step of removing liquid from said processing chamber.

10. The method of claim 8, further comprising a step of dispensing and aspirating a washing liquid to said processing chamber.

11. The method of claim 8, further comprising mixing any liquid in said processing chamber.

12. The method of claim 11, wherein said mixing is done by vortex shaking.

13. A diagnostic instrument for determining the presence of an analyte in a sample comprising:
   one or more devices according to claim 1,
   a module for entering a sample into said device, and
   a module for determining the results of the reaction of analytes in said sample with said reagents.

* * * * *